United States Patent

Rohrmann et al.

[11] Patent Number: 5,932,669
[45] Date of Patent: Aug. 3, 1999

[54] METALLOCENES HAVING BENZO-FUSED INDENYL DERIVATIVES AS LIGANDS, PROCESSES FOR THEIR PREPARATION AND THEIR USE AS CATALYSTS

[75] Inventors: Jürgen Rohrmann; Volker Dolle, both of Kelkheim; Andreas Winter, Glashütten; Frank Küber, Oberursel, all of Germany

[73] Assignee: Targor GmbH, Germany

[21] Appl. No.: 08/470,340

[22] Filed: Jun. 6, 1995

Related U.S. Application Data

[62] Division of application No. 08/373,862, Jan. 17, 1995., Pat. No. 5,455,366, which is a continuation of application No. 08/291,078, Aug. 17, 1994., abandoned, which is a continuation of application No. 07/980,992, Nov. 24, 1992., abandoned

[30] Foreign Application Priority Data

Nov. 30, 1991 [DE] Germany .................. P 41 39 596

[51] Int. Cl.$^6$ .................................... C08F 4/642
[52] U.S. Cl. .................. 526/160; 526/127; 526/134; 526/943; 526/150; 502/117; 502/103
[58] Field of Search ................... 526/127, 134, 526/160, 943; 502/103, 117

[56] References Cited

U.S. PATENT DOCUMENTS

| | | | |
|---|---|---|---|
| 4,769,510 | 9/1988 | Kaminsky et al. | 585/512 |
| 4,892,851 | 1/1990 | Ewen et al. | 502/104 |
| 4,931,417 | 6/1990 | Miya et al. | 502/117 |
| 5,017,714 | 5/1991 | Welborn, Jr. | 556/12 |
| 5,087,677 | 2/1992 | Brenkner et al. | 526/160 |
| 5,103,030 | 4/1992 | Rohrmann et al. | 556/12 |
| 5,145,819 | 9/1992 | Winter et al. | 502/117 |
| 5,243,001 | 9/1993 | Winter et al. | 526/127 |
| 5,276,208 | 1/1994 | Winter et al. | 556/53 |
| 5,296,434 | 3/1994 | Karl et al. | 502/117 |
| 5,324,800 | 6/1994 | Welborn, Jr. | 526/160 |
| 5,329,033 | 7/1994 | Spaleck et al. | 556/53 |
| 5,514,760 | 5/1996 | Karl et al. | 526/127 |
| 5,561,093 | 10/1996 | Fujita et al. | 502/117 |

FOREIGN PATENT DOCUMENTS

| | | |
|---|---|---|
| 0 129 368 | 12/1984 | European Pat. Off. . |
| 0 185 918 | 7/1985 | European Pat. Off. . |
| 0284708 | 10/1988 | European Pat. Off. . |
| 0 316 155 | 5/1989 | European Pat. Off. . |
| 0 320 762 | 6/1989 | European Pat. Off. . |
| 0 336 128 | 10/1989 | European Pat. Off. . |
| 0 344 887 | 12/1989 | European Pat. Off. . |
| 0 351 392 | 1/1990 | European Pat. Off. . |
| 0 355 289 | 2/1990 | European Pat. Off. . |
| 0 366 290 | 5/1990 | European Pat. Off. . |
| 0 407 870 | 1/1991 | European Pat. Off. . |
| 0 426 643 | 5/1991 | European Pat. Off. . |
| 0 433 990 | 6/1991 | European Pat. Off. . |
| 442 725 | 8/1991 | European Pat. Off. . |
| 0 485 821 | 5/1992 | European Pat. Off. . |
| 0 485 823 | 5/1992 | European Pat. Off. . |
| 0 500 005 | 8/1992 | European Pat. Off. . |
| 0 529 908 | 3/1993 | European Pat. Off. . |
| 37 26 067 | 2/1989 | Germany . |

OTHER PUBLICATIONS

Spaleck et al., New J. Chem., "Stereorigid Metallocenes: Correlations Between Structure and Behaviour in Homopolymerizations of Propylene", vol. 14, pp. 499–403 (1990).

Röll, V.W., et al., Angew. Chem., "Stereo–und Regioselektivitat von chiralen, alkylsubstituierten ansa–Zirconocen–Katalysatoren bei der Methylalumoxan–aktivierten Propen––Polymerization", vol. 102, No. 3, pp. 339–341 (1990).

Piccoliovazzi, N. et al., Organometallics, "Eelectronic Effects in Homogeneous Indenylzirconium Ziegler–Natta Catalysts", vol. 9; pp. 3098–3105 (1990).

Miyamota, T.K., et al., Chemistry Letters, The Chemical Society of Japan, "A Bulky Ligand and its Organometallic Compound: Synthesis of Heptamethylidene and a Ferrocene–Type Complex, Fe ($n^5$ —$C_9Me_7$)$_2$"pp. 729–730 (1981).

Esperas, S., Acta Chemica Scandinavica, "The Crystal and Molecular Structure of Cyano(methylisocyanide)gold(I )", A 30, No. 7, pp. 527–530 (1976).

Adcock et al., Austr. J. Chem., vol. 29, "Substituent Effects by $^{19}$F Nuclear Magnetic Resonace: Polar and π–Electron Effects", pp. 2571–2581.

(List continued on next page.)

Primary Examiner—Mark Nagumo
Attorney, Agent, or Firm—Connolly & Hutz

[57] ABSTRACT

A very effective catalyst system for olefin polymerization comprises a cocatalyst, preferably an aluminoxane, and a metallocene of the formula I

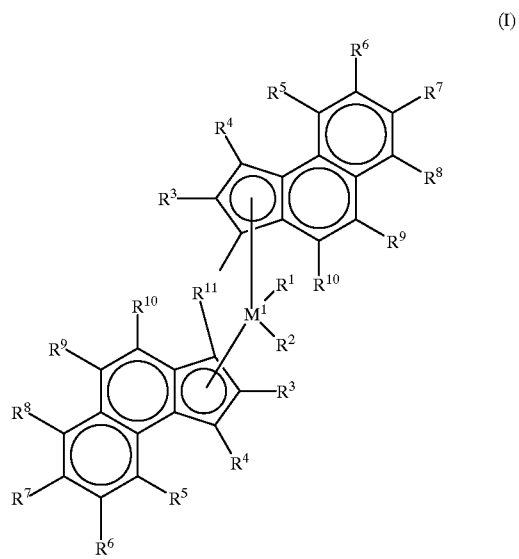

in which, preferably,
$M^1$ is Zr or Hf, $R^1$ and $R^2$ are halogen or alkyl, $R^3$ is alkyl, $R^4$ to $R^{10}$ are alkyl or hydrogen and $R^{11}$ is a (substituted) alkylene or heteroatom bridge.

20 Claims, No Drawings

OTHER PUBLICATIONS

Marechal et al., *Bull. Soc. Chim. Fr. 6*, "Homopolymerisation cationlique des dimethyl–4,7,dimethyl–4,6 et dimethyl–5,6 indenes",No. 348, pp. 1981–2039, (1969).

Chemical Abstracts 90:567 103691p; (1978).

Criegee et al., *Chem. Ber., vol. 94*, "Uber den Nickelkomplex $C_{18}H_{22}$Ni und den daraus gewonnenen Kohlenwasserstoff $C_{13}H_{18}$", pp. 3461–3468 (1964).

Hart et al., Notes, *J. Am. Chem. Soc.*, vol. 72, "Acylation–Alkylation Studies", pp. 3286–3287 (1950).

Katz, Thomas J., *J. Am. Chem. Soc.*, "Asymmetric Synthesis of Helical Metallocenes", vol. 108, 1986, pp. 179–181.

Ewen, J.A., et al, *J. Am. Chem. Soc.,* Crystal Structures and Sterospecific Propylene Polymerizations with Chiral Hafnium Metallocene Catalysts, vol. 109, 1987, pp. 6544–6545.

Bulletin De La Societe Chimique De France, "Etude de monomeres halogenes et de leur polymerisation cationique", No. 11, pp. 3092–3095, (1973).

J. Org. Chem., "*Friedel–Crafts reactions of Ethyl Cyclopropanecarboxylate*", vol. 46, pp. 3758–3760 (1981).

Soga, K. et al., Macromolecules, "*Perfect Conversion of Aspecific Sites into Isopecific Sites in Ziegler–Natta Catalysts*", vol. 22, pp. 3824–3826 (1989).

J. Org. Chem., "*Friedel–Crafts Chemistry. A Mechanistic Study of the Reaction of 3–Choloro–4'–fluoro–2–methylpropiophenone with $ALCL_3$ and $ALCL_3$–$CH_3NO_2$*", nol. 43, No. 16, pp. 3126–3131 (1978).

METALLOCENES HAVING BENZO-FUSED INDENYL DERIVATIVES AS LIGANDS, PROCESSES FOR THEIR PREPARATION AND THEIR USE AS CATALYSTS

This application is a divisional of application Ser. No. 08/373,862 filed Jan. 17, 1995, now U.S. Pat. No. 5,455,366 which is a continuation application of Ser. No. 08/291,078 filed Aug. 17, 1994, abandoned which, in turn is a continuation of Ser. No. 07/980,992 filed Nov. 24, 1992, abandoned.

The present invention relates to novel metallocenes having benzo-fused indenyl derivatives as ligands, which can be used very advantageously as catalyst components in the preparation of polyolefins of high isotacticity, narrow molecular weight distribution and high molecular weight.

Polyolefins of high molecular weight are of particular importance for the production of films, sheets or large hollow articles, such as, for example, pipes or moldings.

The preparation of polyolefins using soluble metallocene compounds in combination with aluminoxanes or other cocatalysts which, because of their Lewis acidity, can convert the neutral metallocene into a cation and can stabilize it, is known from the literature.

For example, a specific preactivation method for the metallocene using an aluminoxane which leads to a considerable increase in the activity of the catalyst system and to a significant improvement in the particle morphology of the polymer has been proposed (cf. DE 37 26 067). Although the preactivation increases the molecular weight, no substantial increase can be achieved.

It has been possible to realize a further but still inadequate increase in the molecular weight by using metallocenes which are specifically bridged by hetero atoms and have a high metallocene activity Catalysts based on ethylenebisindenylhafnium dichloride and ethylene-bis(4,5,6,7-tetrahydro-1-indenyl)hafnium dichloride and methylaluminoxane, with which higher molecular weight polypropylenes can be prepared by suspension polymerization, furthermore are known (cf. J. A. Ewen et al., J. Am. Chem. Soc. 109 (1987) 6544). However, under industrially relevant polymerization conditions, the particle morphology of the polymers produced in this way is unsatisfactory and the activity of the catalysts employed is comparatively low. Associated with the high catalyst costs, inexpensive polymerization is thus not possible with these systems.

It has been possible to achieve a significant increase in the molecular weight by using metallocenes in which the aromatic πII-ligands, which are fixed by a bridge, carry substituents in the 2-position (DE-P 40 35 886.0) or in the 2- and 4-position (DE-P 41 28 238.8).

Under the constraint of inexpensive production on a large industrial scale, polymerization must be carried out at the highest possible reaction temperatures, since at higher polymerization temperatures, the heat of polymerization formed can be removed with less cooling medium and the polymerization can therefore be realized with significantly smaller dimensions of the cooling water circulation.

The metallocenes mentioned last, with substituents in the 2- or 2- and 4-position relative to the bridge, are already very efficient in this respect at a polymerization temperature of 70° C., but the molecular weights which can be achieved at industrially relevant polymerization temperatures (for example 70° C.) are still too low for many industrial uses, such as, for example, the preparation of polymers for pipes and large hollow articles, as well as specific fibers.

There was the object of the discovering a process or a catalyst system which produces polymers of good particle morphology and high molecular weight in a high yield. The entire range of molecular weight can be covered by only one metallocene by using hydrogen as the molecular weight regulator.

Surprisingly, it has now been found that metallocenes having specific indenyl derivatives as ligands are suitable catalysts (catalyst components) in the preparation of, in particular, isotactic polyolefins of high molecular weight.

The present invention therefore relates to the compounds of the following formula I

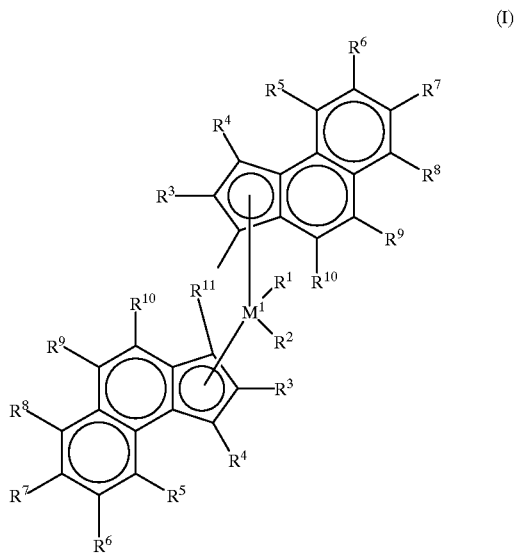

(I)

in which
M$^1$ is a metal of group IVb, Vb or VIb of the periodic table,
R$^1$ and R$^2$ are identical or different and are a hydrogen atom, a C$_1$–C$_{10}$-alkyl group, a C$_1$–C$_{10}$-alkoxy group, a C$_6$–C$_{10}$-aryl group, a C$_6$–C$_{10}$-aryloxy group, a C$_2$–C$_{10}$-alkenyl group, a C$_7$–C$_{40}$-arylalkyl group, a C$_7$–C$_{40}$-alkylaryl group, a C$_8$–C$_{40}$-arylalkenyl group, an OH group or a halogen atom,
the radicals R$^3$ are identical or different and are a hydrogen atom, a halogen atom, a C$_1$–C$_{10}$-alkyl group, which can be halogenated, a C$_6$–C$_{10}$-aryl group or an —NR$_2$, —SR, —OSiR$_3$, —SiR$_3$ or —PR$_2$ radical, in which R is a halogen atom, a C$_1$–C$_{10}$-alkyl group or a C$_6$–C$_{10}$-aryl group,
R$^4$ to R$^{10}$ have the meaning given for R$^3$, or adjacent radicals R$^4$ to R$^{10}$, with the atoms joining them, form an aromatic or aliphatic ring, and $R^{11}$ is

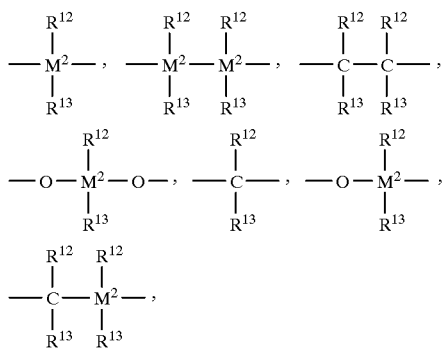

$=BR^{12}$, $=AlR^{12}$, —Ge—, —Sn—, —O—, —S—, $=SO$, $=SO_2$, $=NR^{12}$, $=CO$, $=PR^{12}$ or $=P(O)R^{12}$
in which $R^{12}$ and $R^{13}$ are identical or different and are a hydrogen atom, a halogen atom, a $C_1$–$C_{10}$-alkyl group, a $C_1$–$C_{10}$-fluoroalkyl group, a $C_6$–$C_{10}$-aryl group, a $C_6$–$C_{10}$-fluoroaryl group, a $C_1$–$C_{10}$-alkoxy group, a $C_2$–$C_{10}$-alkenyl group, a $C_7$–$C_{40}$-arylalkyl group, a $C_8$–$C_{40}$-arylalkenyl group or a $C_7$–$C_{40}$-alkylaryl group, or $R^{12}$ and $R^{13}$, in each case with the atoms joining them, form a ring, and $M^2$ is silicon, germanium or tin.

Alkyl is straight-chain or branched alkyl, and halogen (halogenated) is fluorine, chlorine, bromine or iodine, preferably fluorine or chlorine.

In spite of having the same designation, the substituents $R^4$ to $R^{10}$ on the two indenyl ligands can be different (cf. definition of $R^3$).

In formula I, $M^1$ is a metal of group IVb, Vb or VIb of the periodic table, for example titanium, zirconium, hafnium, vanadium, niobium, tantalum, chromium, molybdenum or tungsten, preferably zirconium, hafnium or titanium.

$R^1$ and $R^2$ are identical or different and are a hydrogen atom, a $C_1$–$C_{10}$-, preferably $C_1$–$C_3$-alkyl group, a $C_1$–$C_{10}$-, preferably $C_1$–$C_3$-alkoxy group, a $C_6$–$C_{10}$-, preferably $C_6$–$C_8$-aryl group, a $C_6$–$C_{10}$-, preferably $C_6$–$C_8$-aryloxy group, a $C_2$–$C_{10}$-, preferably $C_2$–$C_4$-alkenyl group, a $C_7$–$C_{40}$-, preferably $C_7$–$C_{10}$-arylalkyl group, a $C_7$–$C_{40}$-, preferably $C_7$–$C_{12}$-alkylaryl group, a $C_8$–$C_{40}$-, preferably $C_8$–$C_{12}$-arylalkenyl group or a halogen atom, preferably chlorine.

The radicals $R^3$ to $R^{10}$ are identical or different and are a hydrogen atom, a halogen atom, preferably a fluorine, chlorine or bromine atom, a $C_1$–$C_{10}$-, preferably $C_1$–$C_4$-alkyl group, which can be halogenated, a $C_6$–$C_{10}$-, preferably $C_6$–$C_8$-aryl group or an —$NR_2$, —$SR$, —$OSiR_3$, —$SiR_3$ or —$PR_2$ radical, in which R is a halogen atom, preferably a chlorine atom, or a $C_1$–$C_{10}$-, preferably $C_1$–$C_3$-aryl group or $C_6$–$C_{10}$-, preferably $C_6$–$C_8$-aryl group.

$R^{11}$ is

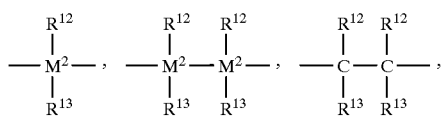

-continued

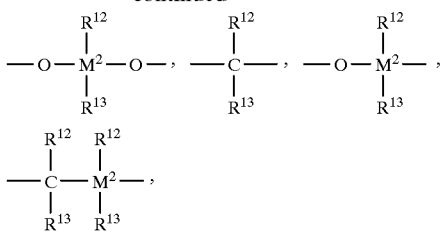

$=BR^{12}$, $=AlR^{12}$, —Ge—, —Sn—, —O—, —S—, $=SO$, $=SO_2$, $=NR^{12}$, $=CO$, $=PR^{12}$ or $=P(O)R^{12}$ in which $R^{12}$ and $R^{13}$ are identical or different and are a hydrogen atom, a halogen atom, a $C_1$–$C_{10}$-, preferably $C_1$–$C_4$-alkyl group, in particular a methyl group, a $C_1$–$C_{10}$-fluoroalkyl group, preferably a $CF_3$ group, a $C_6$–$C_{10}$-, preferably $C_6$–$C_8$-aryl group, a $C_6$–$C_{10}$-fluoroaryl group, preferably a pentafluorophenyl group, a $C_1$–$C_{10}$-, preferably $C_1$–$C_4$-alkoxy group, in particular a methoxy group, a $C_2$–$C_{10}$-, preferably $C_2$–$C_4$-alkenyl group, a $C_7$–$C_{40}$-, preferably $C_7$–$C_{10}$-arylalkyl group, a $C_8$–$C_{40}$-, preferably $C_8$–$C_{12}$-arylalkenyl group or a $C_7$–$C_{40}$-, preferably $C_7$–$C_{12}$-alkylaryl group, or $R^{12}$ and $R^{13}$, in each case together with the atoms joining them, form a ring.

$M^2$ is silicon, germanium or tin, preferably silicon or germanium.

For compounds of the formula I, preferably, $M^1$ is zirconium or hafnium, $R^1$ and $R^2$ are identical and are a $C_1$–$C_3$-alkyl group or a halogen atom, the radicals $R^3$ are identical and are a $C_1$–$C_4$-alkyl group, $R^4$ to $R^{10}$ are identical or different and are hydrogen or are a $C_1$–$C_4$-alkyl group and $R^{11}$ is

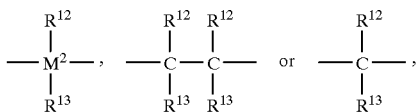

in which $M^2$ is silicon and $R^{12}$ and $R^{13}$ are identical or different and are a $C_1$–$C_4$-alkyl group or a $C_6$–$C_{10}$-aryl group.

Compounds I which are furthermore preferred are those in which the radicals $R^4$ and $R^{10}$ are hydrogen and $R^5$–$R^9$ are a $C_1$–$C_4$-alkyl group or hydrogen.

In particular, $M^1$ is zirconium, $R^1$ and $R^2$ are identical and are chlorine, the radicals $R^3$ are identical and are a $C_1$–$C_4$-alkyl group, $R^4$ and $R^{10}$ are hydrogen, $R^5$ to $R^9$ are identical or different and are a $C_1$–$C_4$-alkyl group or hydrogen and $R^{11}$ is

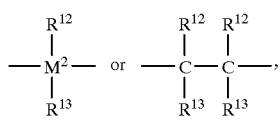

in which $M^2$ is silicon and $R^{12}$ and $R^{13}$ are identical or different and are a $C_1$–$C_4$-alkyl group or a $C_6$–$C_{10}$-aryl group.

Particularly preferred compounds of the formula I are those in which $M^1$ is zirconium, $R^1$ and $R^2$ are chlorine, $R^3$ is methyl, $R^4$ to $R^{10}$ are hydrogen and $R^{11}$ is

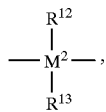

in which $M^2$ is silicon and $R^{12}$ and $R^{13}$ are identical or different and are methyl or phenyl; in particular the compounds I mentioned in the embodiment examples.

The present invention furthermore relates to a process for the preparation of a compound of the formula I, which comprises reacting a compound of the formula IV

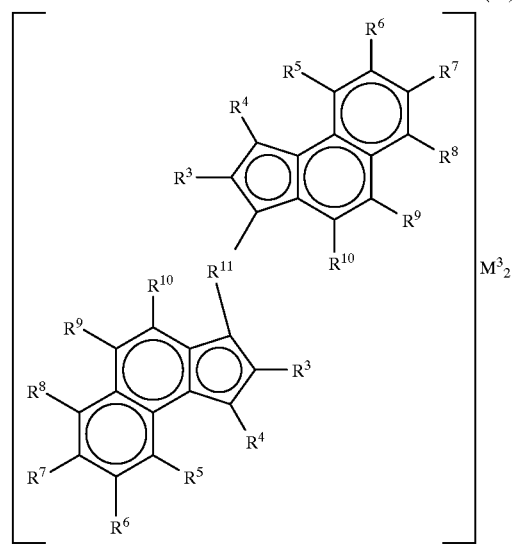

in which the radicals $R^3$ to $R^{11}$ have the meanings given in formula I and $M^3$ is an alkali metal, preferably lithium, with a compound of the formula V $$M^1X_4 \qquad (V)$$

in which $M^1$ has the meaning given in formula I and X is a halogen atom, preferably chlorine, and if appropriate derivatizing the resulting reaction product.

The preparation of the metallocenes I is carried out by processes which are known from the literature, and is represented in the following equation (cf. furthermore the embodiment examples):

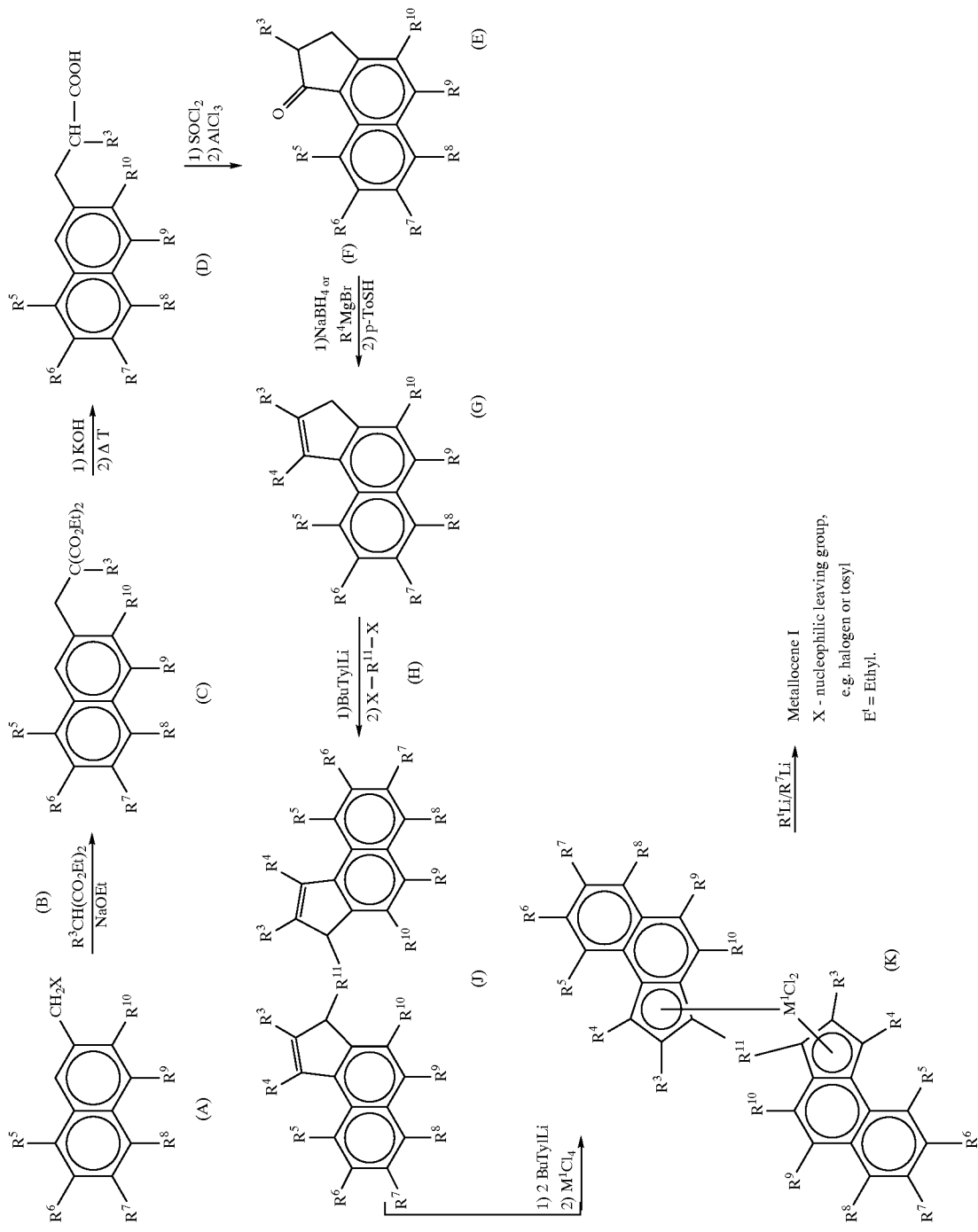

The naphthalene derivatives of the formula A are commercially obtainable or can be prepared by methods which are known from the literature ("Friedel Crafts and Related Reactions", Wiley, New York, 1964, Vol. II, pages 659–766, Bull. Soc. Chim. Belges, 58 (1949) 87, and J. Amer. Chem. Soc. 89 (1967) 2411).

The reaction to give the compounds of the formula C is carried out by methods which are known from the literature, by reaction with substituted malonic acid esters of the formula B under basic conditions, such as, for example, in ethanolic solutions of sodium ethanolate (J. Org. Chem. 23 (1958) 1441, and J. Am. Chem. Soc. 70 (1948) 3569).

The compounds of the formula C are hydrolyzed with alkali metal hydroxides such as potassium hydroxide or sodium hydroxide by methods which are known from the literature, and decarboxylated by thermolysis of the resulting dicarboxylic acid by methods which are known from the literature to give the compounds of the formula D (J. Org. Chem. 23 (1958) 1441, and J. Am. Chem. Soc. 70 (1948) 3569).

The cyclization to give the substituted benzoindanones of the formula E is carried out by methods which are known from the literature, by reaction with chlorinating reagents, such as, for example, $SOCl_2$, to give the corresponding acid chlorides and subsequent cyclization with a Friedel-Crafts catalyst in an inert solvent, such as, for example, with $AlCl_3$ or polyphosphoric acid in methylene chloride or $CS_2$ (Organometallics 9 (1990) 3098, Bull. Soc. Chim. Fr. 3 (1967) 988, and J. Org. Chem. 49 (1984) 4226).

The reaction to give the benzoindene derivatives of the formula G is carried out by methods which are known from the literature, by reduction with sodium borohydride or lithium aluminum hydride in an inert solvent, such as, for example, diethyl ether or tetrahydrofuran, or by alkylation with alkylating agents of the formula F or with lithiumalkyls to give the corresponding alcohols and dehydration of the alcohols under acid conditions, such as, for example, with p-toluenesulfonic acid or oxalic acid or by reaction with dehydrating substances, such as magnesium sulfate or molecular sieves (Organometallics 9 (1990) 3098, Acta Chem. Scand. B 30 (1976) 527, and J. Amer. Chem. Soc. 65 (1943) 567).

Benzoindene derivatives of the formula G can also be built up in 4 synthesis steps by another synthesis route, which is not shown in more detail here, starting from substituted naphthalenes (Bull. Soc. Chim. Fr. 3 (1967) 988).

The preparation of the ligand systems of the formula J and the reaction to give the bridged chriral metallocenes of the formula K, as well as the isolation of the desired racemic form, are known in principle (Au-A-31478/89, J. Organomet. Chem. 342 (1988) 21, EP 0 284 707 and EP 0 320 762). For this, the benzoindene derivative of the formula G is deprotonated with strong bases, such as, for example, butyllithium, in an inert solvent and reacted with a reagent of the formula H to give the ligand system of the formula J. This is then deprotonated (compound of the formula IV) with two equivalents of a strong base, such as, for example, butyllithium, in an inert solvent and reacted with the corresponding metal tetrahalide, such as, for example, zirconium tetrachloride, in a suitable solvent. Suitable solvents are aliphatic or aromatic solvents, such as, for example, hexane or toluene, ethereal solvents, such as, for example, tetrahydrofuran or diethyl ether, or halogenated hydrocarbons, such as, for example, methylene chloride. The racemic form and the meso form are separated by extraction or recrystallization with suitable solvents.

The derivatization to give the metallocenes of the formula I can be carried out by methods which are known from the literature, for example by reaction with alkylating agents, such as, for example, methyllithium (Organometallics 9 (1990) 1539, J. Amer. Chem. Soc. 95 (1973) 6263, and EP 0 277 004).

The metallocenes I according to the invention are highly active catalyst components for olefin polymerization.

The present invention thus also relates to a process for the preparation of an olefin polymer by polymerization or copolymerization of an olefin of the formula $R^a$—CH=CH—$R^b$, in which $R^a$ and $R^b$ are identical or different and are a hydrogen atom or a hydrocarbon radical having 1 to 14 carbon atoms, or $R^a$ and $R^b$, with the atoms joining them, can form a ring, at a temperature of from −60 to 200° C., under a pressure of from 0.5 to 100 bar, in solution, in suspension or in the gas phase, in the presence of a catalyst which is formed from a metallocene, as the transition metal compound, and a cocatalyst, which comprises using a compound of the formula I as the metallocene.

The chiral metallocenes are preferably employed as the racemate. However, the pure R- or S-form can also be used. Optically active polymer can be prepared using these pure stereoisomeric forms. However, the meso form of the metallocenes should be removed, since the polymerization-active center (the metal atom) in these compounds is no longer chiral, because of mirror symmetry on the central metal, and therefore cannot produce a highly isotactic polymer. If the meso form is not removed, atactic polymer is also formed, alongside isotactic polymer. For certain uses—flexible shaped articles, for example—this may be entirely desirable.

The separation of the stereoisomers is known in principle.

According to the invention, an aluminoxane of the formula II

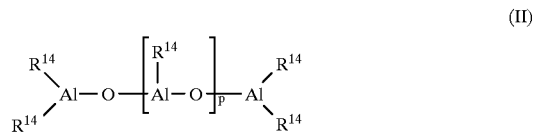

(II)

for the linear type, and/or of the formula (III)

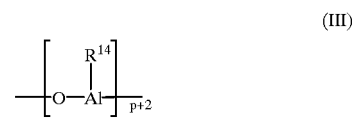

(III)

for the cyclic type, in which, in the formulae (II) and (III), the radicals $R^{14}$ can be identical or different and are a $C_1$–$C_6$-alkyl or a $C_6$–$C_{18}$-aryl group, benzyl or hydrogen and p is an integer from 2 to 50, preferably 10 to 35, is preferably used as the cocatalyst.

Preferably, the radicals $R^{14}$ are identical and are methyl, isobutyl, phenyl or benzyl, particularly preferably methyl.

If the radicals $R^{14}$ are different, they are preferably methyl and hydrogen, or alternatively methyl and isobutyl, hydrogen or isobutyl preferably being present to the extent of 0.01–40% (number of radicals $R^{14}$).

The aluminoxane can be prepared in various ways by known processes. One of the methods is, for example, to react an aluminum-hydrocarbon compound and/or hydridoaluminum-hydrocarbon compound with water (gaseous, solid, liquid or bonded—for example as water of crystallization) in an inert solvent (such as, for example, toluene). To prepare an aluminoxane having different alkyl groups $R^{14}$, two different aluminum trialkyls ($AlR_3+AlR'_3$) corresponding to the desired composition, are reacted with water (cf. S. Pasynkiewicz, Polyhedron 9 (1990) 429 and EP-A 302 424).

The precise structure of the aluminoxanes II and III is not known.

Depending on the nature of the preparation, all the aluminoxane solutions have the common feature of a varying content of unreacted aluminum starting compound, which is present in the free form or as an adduct.

It is possible for the metallocene to be preactivated with an aluminoxane of the formula (II) and/or (III) before use in the polymerization reaction. In this way, the polymerization activity is significantly increased and the particle morphology is improved.

The preactivation of the transition metal compound is carried out in solution. Preferably, in this procedure, the metallocene is dissolved in a solution of the aluminoxane in an inert hydrocarbon. An aliphatic or aromatic hydrocarbon is a suitable inert hydrocarbon. Toluene is preferably used.

The concentration of the aluminoxane in the solution is in the range from about 1% by weight up to the saturation limit, preferably from 5 to 30% by weight, in each case based on the total solution. The metallocene can be employed in the same concentration, but it is preferably employed in an amount of $10^{-4}$–1 mol per mol of aluminoxane. The preactivation time is 5 minutes to 60 hours, preferably 5 to 60 minutes. The preactivation is carried out at a temperature of from $-78°$ C. to $100°$ C., preferably 0 to $70°$ C.

The metallocene can also be prepolymerized or applied to a support. The (or one of the) olefin(s) employed in the polymerization is (are) preferably used for the prepolymerization.

Suitable supports are, for example, silica gels, aluminum oxides, solid aluminoxane or other inorganic support materials. A polyolefin powder in finely divided form is also a suitable support material.

According to the invention, compounds of the formulae $R_xNH_{4-x}BR'_4$, $R_xPH_{4-x}BR'_4$, $R_3CBR'_4$ or $BR'_3$ can be used as suitable cocatalysts instead of or alongside an aluminoxane. In these formulae, x is a number from 1 to 4, preferably 3, the radicals R are identical or different, preferably identical, and are $C_1$–$C_{10}$-alkyl or $C_6$–$C_{18}$-aryl, or two radicals R, together with the atom joining them, form a ring, and the radicals R' are identical or different, preferably identical, and are $C_6$–$C_{18}$-aryl, which can be substituted by alkyl, haloalkyl or fluorine.

In particular, R is ethyl, propyl, butyl or phenyl and R' is phenyl, pentafluorophenyl, 3,5-bistrifluoromethylphenyl, mesityl, xylyl or tolyl (cf. EP-A 277 033, EP-A 277 004 and EP-A 426 638).

If the abovementioned cocatalysts are used, the actual (active) polymerization catalyst comprises the reaction product of the metallocene and one of the compounds mentioned. This reaction product is therefore preferably first prepared outside the polymerization reactor in a separate step, using a suitable solvent.

In principle, any compound which, on the basis of its Lewis acidity, can convert the neutral metallocene into a cation and can stabilize the latter ("labile coordination") is suitable according to the invention as a cocatalyst. Moreover, the cocatalyst, or the anion formed from it, should not undergo further reactions with the metallocene cation formed (cf. EP-A 427 697).

To remove catalyst poisons present in the olefin, purification with an aluminum alkyl, for example $AlMe_3$ or $AlEt_3$, is advantageous. This purification either can be carried out in the polymerization system itself, or the olefin is brought into contact with the Al compound before addition into the polymerization system, and is then separated off again.

The polymerization or copolymerization is carried out in a known manner in solution, in suspension or in the gas phase, continuously or discontinuously, in one or more stages at a temperature of from $-60$ to $200°$ C., preferably 30 to $80°$ C., particularly preferably 50 to $80°$ C. Olefins of the formula $R^a$—CH=CH—$R^b$ are polymerized or copolymerized. In this formula, $R^a$ $R^b$ are identical or different and are a hydrogen atom or an alkyl radical having 1 to 14 carbon atoms. However, $R^a$ and $R^b$, with the carbon atoms joining them, can also form a ring. Examples of such olefins are ethylene, propylene, 1-butene, 1-hexane, 4-methyl-1-pentene, 1-octene, norbornene or norbonadiene. In particular, propylene and ethylene are polymerized.

If necessary, hydrogen is added as a molecular weight regulator and/or to increase the activity. The overall pressure in the polymerization system is 0.5 to 100 bar. Polymerization in the pressure range of 5 to 64 bar, which is of particular industrial interest, is preferred.

The metallocene is used here in a concentration, based on the transition metal, of $10^{-3}$ to $10^{-8}$, preferably $10^{-4}$ to $10^{-7}$ mol of transition metal per $dm^3$ of solvent or per $dm^3$ of reactor volume. The aluminoxane is used in a concentration of $10^{-5}$ to $10^{-1}$ mol, preferably $10^{-4}$ to $10^{-2}$ mol per $dm^3$ of solvent or per $dm^3$ of reactor volume. The other cocatalysts mentioned are used in approximately equimolar amounts to the metallocene. In principle, however, higher concentrations are also possible.

If the polymerization is carried out as suspension or solution polymerization, an inert solvent customary for the Ziegler low pressure process is used. For example, the polymerization is carried out in an aliphatic or cycloaliphatic hydrocarbon; examples of these which may be mentioned are propane, butane, pentane, hexane, heptane, isooctane, cyclohexane and methylcyclohexane.

A gasoline or hydrogenated diesel oil fraction furthermore can be used. Toluene can also be used. The polymerizaton is preferably carried out in the liquid monomer.

If inert solvents are used, the monomers are metered into the reaction vessel in gaseous or liquid form.

The polymerization can be of any desired length, since the catalyst system to be used according to the invention shows only a slight drop in polymerization activity with respect to time.

The process according to the invention is distinguished by the fact that the metallocenes described produce polymers of high molecular weight, high stereospecificity and good particle morphology in the temperature range of between 50 and 80° C., which is of particular industrial interest.

In particular, the zirconocenes according to the invention advance into a molecular weight range, or even exceed it, which was reserved for the hafnocenes in the prior art to date. However, these hafnocenes had the disadvantage of only a low polymerization activity and very high catalyst costs, and the polymers produced with them had a poor powder morphology.

The following examples are intended to illustrate the invention in more detail.

The abbreviations have the following meanings:

| | | |
|---|---|---|
| VN | = viscosity number in cm$^3$/g | |
| $M_w$ | = weight-average molecular weight in g/mol | determined by gel permeation chromatography |
| $M_w/M_n$ | = polydispersity | |
| m.p. | = melting point, determined by differential scanning calorimetry (20° C./minute heating up/ cooling down rate) | |
| II | = isotactic index (II = mm + ½ mr), determined by $^{13}$C-NMR spectroscopy | |
| MFI/(230/5) | = melt flow index, measured in accordance with DIN 53735; in dg/min | |
| BD | = polymer bulk density in g/dm$^3$ | |

Synthesis of the metallocenes I used in the polymerization examples

EXAMPLE A

Synthesis of rac-dimethylsilanediylbis(2-methyl-4, 5-benzoindenyl)-zirconium dichloride 1. Diethyl methyl(2-naphthylmethyl)malonate (1)

5.15 g (224 mmol) of sodium were dissolved in 150 ml of absolute ethanol, while heating, and 37.3 ml (217 mmol) of diethyl methylmalonate were added at room temperature. A solution of 50 g (217 mmol) of 2-bromomethylnaphthalene (96% pure) in 270 ml of ethanol was slowly added dropwise at 0° C., and the mixture was heated under reflux for a further 4 to 5 hours. It was poured onto ice-water and extracted with ethyl acetate. The combined organic phases were dried with sodium sulfate and evaporated. After drying under an oil pump vacuum, the oily residue was stirred with hexane at 0° C., whereupon 55 g (81%) of the compound 1 crystallized.

2. 2-Methyl-3-naphthylpropionic acid (2)

A solution of 23.7 g (422 mmol) of potassium hydroxide in 50 ml of water was added to 33.2 g (105 mmol) of the compound 1 in 70 ml of ethanol, and the mixture was heated under reflux for 4 hours. After the solvent had been stripped off, the solid residue was taken up in ethyl acetate, water was added and the pH was brought to 1 with hydrochloric acid. The aqueous phase was extracted several times with ethyl acetate. After drying over magnesium sulfate, the combined organic phases were evaporated completely. The residue was stirred with hexane for crystallization. For decarboxylation, the beige-colored solid was heated at 175° C. until the evolution of gas had ended. 21 g (94%) of the product 2 were obtained as a beige-colored solid.

3. 2-Methyl-6,7-benzoindan-1-one (3)

22 ml of thionyl chloride were added to 21 g (98 mmol) of the compound 2, with exclusion of moisture, and the mixture was heated under reflux for 30 minutes. Excess thionyl chloride was then distilled off. The residue was briefly freed from volatile compounds under an oil pump vacuum and then dissolved in 25 ml of methylene chloride, under Ar as an inert gas. The solution was slowly added dropwise to a suspension of 26 g (196 mmol) of aluminum trichloride in 60 ml of methylene chloride and the mixture was heated under reflux for a further 30 minutes. It was poured onto ice and extracted with methylene chloride. The combined organic phases were dried with sodium sulfate and evaporated. The dark oily residue was chromatographed on 600 g of silica gel 60. 8.6 g (45%) of the compound 3 were able to be eluted (yellowish solid) with a mobile phase mixture of hexane/ethyl acetate (9:3).

4. 2-Methyl-4,5-benzoindene (4)

2.2 g (59.5 mmol) of sodium borohydride were added in portions to a solution of 7.8 g (39.7 mmol) of the indanone 3 in 400 ml of a tetrahydrofuran/methanol mixture (2:1) at room temperature, and the mixture was stirred for 14 hours. The solution was poured onto HCl-acid ice and extracted with ether. The combined organic phases were washed several times with water and dried with sodium sulfate. The orange-coloured oil which remained after the solvent had been stripped off was dissolved in 240 ml of toluene, and the solution was heated at 80° C. with 570 mg (3.15 mmol) of p-toluenesulfonic acid for 15 minutes. It was washed several times with water at room temperature, dried with sodium sulfate and evaporated. The residue was chromatographed on 300 g of silica gel 60. 4.7 g (65%) of the indene 4 were able to be eluted (colorless oil) with a mobile phase mixture of hexane/diisopropyl ether (20:1).

$^1$H-NMR spectrum (360 MHz, CDCl$_3$): 8.02 (1,d), 7.84 (1,m), 7.59 (1,d), 7.52 (1,d), 7.38–7.48 (2,m), 7.06 (1,m), 3.42 (2,s), 2.25 (3,d).

5. Dimethylbis(2-methyl-4,5-benzoindenyl)silane (5)

10.2 ml (25.5 mmol) of a 2.5 M butyllithium solution in hexane were added to a solution of 4.6 g (25.5 mmol) of the indene 4 in 50 ml of tetrahydrofuran at room temperature, and the mixture was heated under reflux for 1 hour. The red solution was then added dropwise to a solution of 1.55 g (12 mmol) of dimethyldichlorosilane in 10 ml of tetrahydrofuran at room temperature, and the mixture was heated under reflux for 5 to 6 hours. The reaction solution was poured onto ice-water and extracted several times with ether. The combined organic phases were dried with sodium sulfate and evaporated, and the residue was dried under an oil pump vacuum. It was chromatographed on 300 g of silic gel 60. 500 mg of unreacted starting substance 4 were initially able to be eluted with a mobile phase mixture of hexane/3% ethyl acetate. The ligand system 5 then followed with the same mobile phase. After the solvent had been stripped off, this ligand system was able to be crystallized (isomers) by stirring with hexane. The yield was 1.7 g (34%, or 44% with respect to the indene 4 reacted).

6. rac-Dimethylsilanediylbis(2-methyl-4,5-benzoindenyl) zirconium dichloride (6)

4.0 ml (10.2 mmol) of a 2.5 M butyllithium solution in hexane were added to a solution of 1.7 g (4.1 mmol) of the ligand system 5 in 20 ml of tetrahydrofuran at room temperature under Ar as an inert gas, and the mixture was stirred at room temperature for 14 hours. The residue which remained after the solvent had been stripped off was dried under an oil pump vacuum and washed with hexane. The pale brown powder thus obtained was dried under an oil pump vacuum at 40 to 50° C. for several hours and added to a suspension of 1.0 g (4.0 mmol) of zirconium tetrachloride in 25 ml of methylene chloride at −78° C. After the mixture had been warmed to room temperature, the solvent was stripped off and the residue was extracted with 20 ml of toluene in order to remove the meso form of the zirconocene 6. The residue of the toluene extract was then extracted with 40 ml of methylene chloride. The solution was concentrated to a small volume and left to crystallize at −35° C. A total of 970 mg (42%) of the zirconocene 6 were able to be isolated in several fractions as the pure racemate.

$^1$H-NMR spectrum of the racemate (300 MHz, CDCl$_3$): 7.96 (2,m), 7.78 (2m,), 7.60 (2,d), 7.48–7.56 (4,m), 7.36 (2,d), 7.27 (2,s,β-Ind-H), 2.37 (6,s,Ind-CH$_3$), 1.36 (6,s,Si—CH$_3$). Mass spectrum: 574 M$^+$, correct disintegration, correct isotope pattern.

EXAMPLE B

Synthesis of rac-dimethylsilanediylbis(2-methyl-α-acenaphthindenyl)zirconium dichloride (10)
(nomenclature analogous to Tebbe et al., J. Amer. Chem. Soc. 72 (1950) 3286)

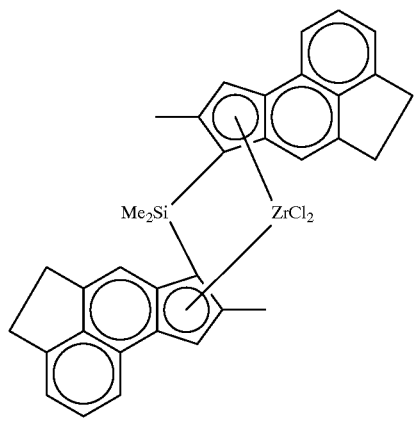

1. 2-Methyl-α-acenaphthindan-1-one (7)

29.7 g (129 mmol) of 2-bromoisobutyryl bromide were added to a solution of 20 g (129 mmol) of α-acenaphthene in 320 ml of methylene chloride at room temperature. 43.5 g (324 mmol) of AlCl$_3$ were then added in the course of 15 minutes, via a solids metering funnel. After the mixture had been stirred for 30 minutes, it as poured onto ice-water and extracted with methylene chloride. The organic phase was washed with water and an NaHCO$_3$ solution and dried with NaSO$_4$. The residue which remained after the solvent had been stripped off was filtered over a short column using silica gel. 25 g (87%) of the indanone 7 were obtained with hexane/ethyl acetate (9:2).

$^1$H-NMR (CDCl$_3$, 100 MHz): 8.57 (d,1), 7.60 (t,1), 7.35 (d,1), 7.25 (s,1), 3.45 (q,1), 3.40 (s,4), 2.60–2.95 (m,2), 1.35 (d,3).

2. 2-Methyl-α-acenaphthindene (8)

A solution of 20 g (90 mmol) of the compound 7 in 250 ml of a tetrahydrofuran/methanol mixture (2:1) was added dropwise to a suspension of 3.8 g (100 mmol) of NaBH$_4$ in 80 ml of tetrahydrofuran. The mixture was stirred at room temperature for 2 hours, and 100 ml of ethyl acetate and 100 ml of half-concentrated HCl were added. The mixture was heated under reflux for 10 minutes and extracted with ethyl acetate. The organic phase was washed with water and dried with NaSO$_4$. On concentrating and cooling to −35° C., a total of 16.3 g (88% of the compound 8 crystallized in several fractions.

3. Dimethylbis(2-methyl-α-acenaphthindenyl)silane (9)

10.8 g (52.4 mmol) of the compound 8 were deprotonated analogously to Example A/5 and reacted with dimethyldichlorosilane. The organic phase was evaporated and the residue was chromatographed on silica gel. 6.2 g (51%) of the ligand system 9 were able to be obtained with hexane/4% ethyl acetate.

$^1$H-NMR (CDCl$_3$, 100 MHz): diastereomer pair 7.1–7.8 (m,aromatic-H), 4.0 (s,CH), 3.45 (s,CH$_2$), 2.47 (d,CH$_3$), 2.40 (d,CH$_3$), −0.25 (s,SiCH$_3$), −0.35 (s,SiCH$_3$), −0.37 (s,SiCH$_3$).

4. rac-Dimethylsilanediylbis(2-methyl-α-acenaphthindenyl)zirconium dichloride (10)

4.9 g (10.5 mmol) of the ligand system 9 were reacted analogously to Example A/6. The crude product, comprising the racemic form with the meso form in a ratio of 1:1, was recrystallized several times from chloroform. 1.3 g (20%) of the racemate 10 were obtained in the form of an orange-yellow powder.

$^1$H-NMR (CDCl$_3$, 100 MHz): 7.0–7.8 (m,aromatic-H), 3.1–3.4 (m,CH$_2$), 2.35 (s,CH$_3$), 1.35 (s,SiCH$_3$)

EXAMPLE C

Synthesis of rac-methylphenylsilanediylbis(2-methyl-4,5-benzoindenyl)zirconium dichloride (12)

1. Methylphenylbis(2-methyl-2,5-benzoindenyl)silane (11)

10.2 ml (25.5 mmol) of a 2.5 M butyllithium solution in hexane were added to a solution of 4.6 g (25.5 mmol) of 2-methyl-4,5-benzoindene (4, Example A/4) in 50 ml of tetrahydrofuran at room temperature under Ar as an inert gas, and the mixture was heated under reflux for 1 hour. The red solution was then added dropwise to a solution of 2.3 g (12 mmol) of methylphenyldichlorosilane in 10 ml of tetrahydrofuran at room temperature, and the mixture was heated under reflux for 8 hours. Working up and purification were carried out analogously to Example A/5. First unreacted starting substance and then 1.4 g (25% with respect to Si) of the ligand system 11 were obtained (isomers) with a mobile phase mixture of hexane/5% ethyl acetate.

2. rac-Methylphenylsilanediylbis(2-methyl-4,5-benzoindenyl)zirconium dichloride (12)

1.2 ml (3 mmol) of a 2.5 M butyllithium solution in hexane were added to a solution of 1.3 g (2.71 mmol) of the ligand 11 in 15 ml of tetrahydrofuran at room temperature under Ar as an inert gas, and the mixture was stirred overnight at room temperature. The solvent was stripped off and the residue, which was extremely sensitive to air, was washed with hexane and dried under an oil pump vacuum for several hours. The powder was added to a suspension of 680 mg (2.9 mmol) of ZrCl$_4$ in 15 ml of CH$_2$Cl$_2$ at −78° C. After the mixture had been warmed slowly to room temperature, it was stirred at this temperature for a further hour and the solvent was stripped off. The residue was first washed with a little toluene and then extracted with $CH_2Cl_2$. On concentrating and cooling slowly to −35° C., 380 mg (22%) of the zirconocene 12 crystallized as the pure racemate (orange-yellow crystalline powder). The mixed fractions which subsequently occurred (racemate and 2 meso forms) were able to be purified by recrystallization several times from chloroform or toluene.

$^1$H-NMR spectrum of the racemate: (100 MHz, $CDCl_3$): 6.8–7.9 (m,aromatic-H), 7.4 (s,α-Ind-H), 2.4 (s,Ind-$CH_3$), 2.1 (Ind-$CH_3$), 1.3 (s,Si—$CH_3$), mass spectrum: 538 M$^+$, correct disintegration, correct isotope pattern.

EXAMPLE D

Synthesis of rac-methylphenylsilanediylbis(2-methyl-α-acenaphthindenyl)zirconium dichloride (14)

1. Methylphenylbis(2-methyl-α-acenaphthindenyl)silane (13)

A solution 10.8 g (52.4 mmol) of 2-methyl-α-acenaphthindene indene (8, Example B/2) in tetrahydrofuran was reacted with 53 mmol of butyllithium and 4.9 g (26 mmol) of methylphenyldichlorosilane analogously to Example A/5. The reaction time was 12 hours. The mixture was worked up analogously. Chromatography with hexane/6% ethyl acetate gave 6.0 g (44%) of the ligand system 13 (isomers).

2. rac-Methylphenylsilanediylbis(2-methyl-α-acenaphthindenyl)zirconium dichloride (14)

5.0 g (9.4 mmol) of the ligand system 13 were reacted with 19.7 mmol of butyllithium and then with 2.2 g (9.4 mmol) of $ZrCl_4$, and the mixture was worked up, analogously to Example A6. The residue was recrystallized several times from methylene chloride to remove the meso forms. 1.2 g (19%) of the metallocene 14 were obtained as the pure racemate in the form of an orange-yellow powder.

$^1$H-NMR ($CDCl_3$, 100 MHz): 6.8–7.8 (m,aromatic-H), 3.0–3.4 (m, $CH_2$), 2.4 (s,$CH_3$), 2.1 (s,$CH_3$), 1.3 (s,Si$CH_3$). Mass spectrum: 690 M$^+$, correct disintegration, correct isotope pattern.

EXAMPLE E

Synthesis of rac-1,2-ethanediylbis(2-methyl-4,5-benzoindenyl)zirconium dichloride (15)

1. 1,2-Bis(2-methyl-4,5-benzoindenyl)ethane (14)

40 ml (100 mmol) of a 2.5 M butyllithium solution in hexane were added to a solution of 18.0 g (100 mmol) of 2-methyl-4,5-benzoindene 4 (Example A/4) in 400 ml of tetrahydrofuran at room temperature, and the mixture was heated under reflux for 30 minutes. 9.35 g (50 mmol) of 1,2-dibromoethane were added at −78° C. The mixture was warmed to room temperature overnight, poured onto ice-water acidified with hydrochloric acid, and extracted with diethyl ether. After the extract had been washed with $NaHCO_3$ solution and dried with $MgSO_4$, the solvent was stripped off and the residue was chromatographed on silica gel 60. After unreacted starting substance and a by-product (spiro compound), 8.6 g (45%) of the ligand system 14 were able to be eluted with hexane/6% ethyl acetate.

2. rac-1,2-Ethanediylbis(2-methyl-4,5-benzoindenyl)-zirconium dichloride (15)

A solution of 4.2 g (10.8 mmol) of the ligand 14 was reacted with butyllithium and $ZrCl_4$ analogously to Example A/6. Extraction of the residue with methylene chloride/toluene and crystallization at −35° C. gave 1.4 g (24%) of the metallocene as the pure racemate in the form of a yellow microcrystalline powder.

$^1$H-NMR spectrum (100 MHz, $CDCl_3$): 7.3–8.0 (m,aromatic-H), 7.1 (s,β-H), 3.4–4.1 (m,$CH_2CH_2$), 2.2 (s,$CH_3$).

Mass spectrum: 546 M$^+$, correct isotope pattern, correct disintegration.

EXAMPLE F

Synthesis of rac-1,2-butanediylbis(2-methyl-4,5-benzoindeyl)zirconium dichloride (17)

1. 1,2-Bis(2-methyl-4,5-benzoindenyl)butane (16)

18.0 g (100 mmol) of 2-methyl-4,5-benzoindene (4, Example A/4) were reacted with 10.7 g (50 mmol) of 1,2-dibromobutane (97% pure), and the mixture was worked up, analogously to Example E/1. Chromatography on silica gel 60 with hexane/2% ethyl acetate gave, after unreacted starting substance and the spiro compound, 3.9 g (19% of the ligand system 16 as an isomer mixture. The individual isomers were able to be separated or enriched by subsequent chromatography on a long column with a mobile phase mixture of hexane and then hexane/1–3% ethyl acetate.

2. rac-1,2-Butanediylbis(2-methyl-4,5-benzoindenyl)-zirconium dichloride (17)

1.0 g (2.41 mmol) of the ligand 16 (2 isomers) were reacted with butyllithium and $ZrCl_4$ analogously to Example A/6. Extraction with toluene/methylene chloride (5:1) and slow crystallization by concentration and cooling to −35° C. gave a total of 0.89 g (65%) of crystal fractions of the metallocene 17 of varying composition of the various isomers of the rac and meso forms (due to the additional chirality center on the bridge). A fraction of the racemate 17 (diastereomer pair) was able to be obtained by a further recrystallization.

Mass spectrum: 574 M$^+$, correct isotope pattern, correct disintegration.

EXAMPLE G

Synthesis of rac-dimethylsilanediylbis(4,5-benzoindenyl)-zirconium dichloride (23)

1. Diethyl 2-naphthylmethylmalonate (18)

34.7 g (217 mmol) of diethylmalonate were reacted and worked up analogously to Example A/1. Treatment with hexane gave 87 g of a brownish oil of the compound 18.

2. 3-Naphthylpropionic acid (19)

87 g of the compound 18 were treated with KOH and thermolyzed analogously to Example A/2. 36 g (83%) of the compound 19 were obtained as a beige-colored powder.

3. 6,7-Benzoindan-1-one (20)

33.6 g (168 mmol) of the compound 19 were reacted with $SOCl_2$ and $AlCl_3$ analogously to Example A/3. The reaction time of the cyclization was 15 minutes at 40° C. Chromatography (partial decomposition on the column) gave 9.4 g (30%) of the indanone 20 as a yellowish solid (partly oil).

$^1$H-NMR spectrum (100 MHz, $CDCl_3$): 9.15 (dd,1, aromatic-H), 7.35–8.1 (m,5,aromatic-H), 3.2 (m,2,$CH_2$), 2.80 (m,$CH_2$).

4. 4,5-Benzoindene (21)

9.4 g (51.6 mmol) of the indanone 20 were reduced analogously to Example A/4. The dehydration was carried out in a distillation apparatus with addition of 6 g of $MgSO_4$. 2.6 g (30%) of the indene 21 passed over at 110° C. under 0.6–0.9 mbar in the form of a colorless distillate, which solidified at room temperature.

$^1$H-NMR spectrum (100 MHz, $CDCl_3$): 7.35–8.2 (m,7, aromatic-H and CH), 6.70 (dt,1,CH), 3.55 (t, $CH_2$).

5. Dimethylbis(4,5-benzoindenyl)silane (22)

3.25 g (19.6 mmol) of the indene 21 were reacted analogously to Example A/5. Chromatography on 600 g of silica gel 60 gave, in addition to the starting substance, 1.8 g (47%) of the ligand system 22 (isomers) with hexane and hexane/ethyl acetate 20:1.

$^1$H-NMR spectrum (100 MHz, $CDCl_3$): 7.3–8.2 (m,aromatic-H), 6.6–6.9 (m,CH), 3.5–4.1 (m,CH), −0.35–0.20 (several singlets, $SiCH_3$).

6. rac-Dimethylsilanediylbis(4,5-benzoindenyl)zirconium dichloride (23)

1.6 g (4.12 mmol) of the ligand 22 were reacted with butyllithium and $ZrCl_4$ analogously to Example A/6. After extraction with methylene chloride, 520 mg (23%) of the metallocene 23 were able to be isolated as the racemate (yellow-orange powder) at −35° C.

$^1$-NMR spectrum (100 MHz, $CDCl_3$): 7.2–8.0 (m,aromatic-H), 7.2 (d,β-CH), 6.4 (d,α-CH), 1.2 (s,$SiCH_3$).

POLYMERIZATION EXAMPLES

Examples 1 and 2

A dry 16 dm$^3$ reactor was flushed with nitrogen and filled with 10 dm$^3$ of liquid propylene. Two thirds of the amount of methylaluminoxane stated in Table 1 were then added as a solution in toluene, and the batch was stirred at 30° C. for 15 minutes.

In parallel, a toluene solution of the metallocene dimethylsilylbis(2-methyl-4,5-benzoindenyl)zirconium dichloride in one third of the stated amount of methylaluminoxane was prepared and the solution was preactivated by being left to stand for 15 minutes. It can also be preactivated by stirring or shaking or in an ultrasonic bath. This solution was then introduced into the reactor, and the polymerization was started by heating to the theoretical temperature. The batch was stopped after one hour by cooling and letting down. The resulting polymer yield and the analytical data determined can be seen from Table 1.

TABLE 1

| Example | Temperature [°C.] | Amount of metallocene [mg] | Amount of MAO [mmol] | Yield [kg] | Activity [kg of PP/g of metallocene × hour] | VN [cm$^3$/g] | MFI/(230/5) [dg/minute] | $M_w/M_n$ | $M_w$ [g/mol] | m.p. [°C.] |
|---|---|---|---|---|---|---|---|---|---|---|
| 1 | 70 | 5.2 | 60 | 2.24 | 431 | 288 | 5.6 | 1.8 | 330,000 | 147 |
| 2 | 50 | 7.3 | 60 | 1.72 | 235 | 444 | 2.4 | 2.0 | 540,000 | 149 |

MAO = methylaluminoxane
PP = polypropylene

Examples 3 and 4

A dry 24 dm$^3$ reactor was flushed with propylene, evacuated and filled with 12 dm$^3$ of liquid propylene. 25 cm$^3$ of a toluene solution of methylaluminoxane (corresponding to 37 mmol of Al, average degree of oligomerization p=18) were then added and the batch was stirred at 30° C. for 15 minutes.

In parallel, the amounts of the metallocene rac-dimethylsilanediylbis(2-methyl-α-acenaphthindenyl)$ZrCl_2$ stated in Table 2 were dissolved in 10 cm$^3$ of a toluene solution of methylaluminoxane (15 mmol of Al), and the solution was preactivated in accordance with Example 1 and employed in the polymerizations. The polymerizations were likewise carried out as described in Example 1. Details of the polymerization and testing of the polymer are to be found in Table 2.

TABLE 2

| Example | mg of metallocene | Polymerization temperature (°C.) | Polymerization time (hours) | Metallocene activity (kg of PP/g of metallocene × hour) | VN (cm$^3$/g) | MFI (230/5) (dg/min) | $M_w$ (g/mol) | $M_w/M_n$ | m.p. (°C.) |
|---|---|---|---|---|---|---|---|---|---|
| 3 | 4.2 | 70 | 1 | 285 | 239 | 16.0 | 248,500 | 2.0 | 149 |
| 4 | 7.1 | 50 | 1.5 | 69.4 | 452 | 1.1 | 521,000 | 2.1 | 150 |

Examples 5 to 9

Example 3 was repeated. However, the metallocenes listed in Table 3 were used. The results of the polymerization are likewise to be found in Table 3.

Example 10

The procedure was as in Example 3, but only 2.6 mg of the metallocene were used, and 2.5 Ndm$^3$ of hydrogen were additionally introduced into the reactor. The metallocene activity was 496 kg of PP/g of metallocene×hour, VN=187 cm$^3$/g, MFI (230/5)=28.5 dg/minute, m.p.=151° C.

Example 11

The procedure was as in Example 10, but the amount of hydrogen was 25 Ndm$^3$. The metallocene activity was 598 kg of PP/g of metallocene×hour, VN=105 cm$^3$/g, m.p. 149° C.

| Example | Metallocene | Metallocene activity [kg PP/g metallocene × hour] | VN [cm³/g] | MFI (230/5) [dg/minute] | $M_w$ [g/mol] | $M_w/M_n$ | m.p. [° C.] |
|---|---|---|---|---|---|---|---|
| 5 | 3.5 mg of rac-Ph(Me)Si-bis(2-methyl-4,5-benzo-indenyl)zirconium dichloride | 236 | 355 | 3.1 | 431,500 | 2.2 | 150 |
| 6 | 4.7 mg of rac-Ph(Me)Si-bis(2-methyl-α-acenaphth-indenyl)zirconium dichloride | 218 | 298 | 4.5 | 330,00 | 2.0 | 148 |
| 7 | 3.0 mg of rac-1,2-Ethane-diylbis(2-methyl-4,5-benzoindenyl)zirconium dichloride | 505 | 198 | 26.5 | 219,000 | 2.3 | 145 |
| 8 | 4.3 mg of rac-1,2-butane-diylbis(2-methyl-4,5-benzoindenyl)zirconium dichloride | 422 | 279 | 5.7 | 321,000 | 2.1 | 146 |
| 9 | 2.8 mg of rac-Me₂Si-bis-(4,5-benzoindenyl)-zirconium dichloride | 438 | 117 | 205 | 124,500 | 2.0 | 141 |

Example 12

The procedure was as in Example 3, but 2.8 mg of the metallocene rac-dimethylsilanediylbis(2-methyl-4,5-benzoindenyl)zirconium dichloride were used and the amount of hydrogen was 15 Ndm³.

The metallocene activity was 647 kg of PP/g of metallocene×hour, VN=147 cm³/g, m.p.=148° C.

Examples 10 to 12 document the good responsiveness to hydrogen for molecular weight regulation in the case of metallocenes according to the invention.

Example 13

A dry 24 dm³ reactor was flushed with propylene and filled with 2.4 Ndm³ of hydrogen and 12 dm³ of liquid propylene. 35 cm³ of a toluene solution of methylaluminoxane (corresponding to 52 mmol of Al, average degree of oligomerization p=19) were then added. In parallel, 3.9 mg of rac-dimethylsilanediylbis(2-methyl-4,5-benzoindenyl) zirconium dichloride were dissolved in 13.5 cm³ of a toluene solution of methylaluminoxane (20 mmol of Al) and the solution was preactivated by being left to stand for 5 minutes.

The solution was then introduced into the reactor, and polymerization was carried out at 60° C. for 1 hour, with continuous addition of 100 g of ethylene. The metallocene activity was 409 kg of polypropylene/g of metallocene× hour, and the ethylene content of the random copolymer was 5.7% by weight.

VN=407 cm³/g, $M_w$=508,500 g/mol, $M_w/M_n$=2.4, m.p.=135° C. According to ¹³C-NMR spectroscopy, the ethylene was incorporated predominantly in isolated form (randomly).

Example 14

A dry 150 dm³ reactor was flushed with nitrogen and filled at 20° C. with 80 dm³ of a dearomatized gasoline cut having a boiling range of 100 to 120° C.

The gas space was then flushed free from nitrogen with propylene, and 50 l of liquid propylene and 64 cm³ of a toluene solution of methylaluminoxane (corresponding to 100 mmol of Al, p=19) were added. The contents of the reactor were heated up to 50° C., and the hydrogen content in the reactor gas space was adjusted to 0.2% by metering in hydrogen, and then later kept constant during the polymerization by subsequent metering-in during the entire polymerization time (checking on-line by gas chromatography).

14.9 mg of rac-dimethylsilanediylbis(2-methyl-4,5-benzoindenyl)zirconium dichloride were dissolved in 32 cm³ of a toluene solution of methylaluminoxane (50 mmol), and the solution was introduced into the reactor.

The polymerization was carried out in a first stage at 65° C. for 6 hours.

In a second stage, 3 kg of ethylene were then added rapidly at 50° C., and after polymerization at this temperature for a further 4 hours, the reaction was stopped with CO₂ gas. 23.9 kg of block copolymer powder were obtained. VN=398 cm³/g, $M_w$=387,500 g/mol, $M_w/M_n$=4.5; MFI (230/5)=14.5 dg/minute.

The block copolymer contained 10.6% by weight of ethylene. Fractionation showed a content of 26.9% by weight of ethylene/propylene rubber. The glass transition temperature of the rubber was −48° C.

Example 15

The procedure was as in Example 10, but 100 Ndm³ of hydrogen were used. The metallocene activity was 605 kg of PP/g of metallocene×hour, the VN was 17 cm³/g and the melting point was 150° C.

Example 15 shows that, with still relatively small amounts of hydrogen, even waxes can be prepared using the metallocenes according to the invention.

We claim:

1. A process for the preparation of an olefin polymer by polymerization or copolymerization of an olefin of the formula $R^a$—CH=CH—$R^b$, in which $R^{11}$ and $R^h$ are identical or different and are a hydrogen atom or a hydrocarbon radical having 1 to 14 carbon atoms, or $R^a$ and $R^b$, with the atoms joining them, can form a ring, in the presence of a catalyst which is formed from a metallocene, as the transition metal compound, and a cocatalyst, which comprises using a compound of the formula I

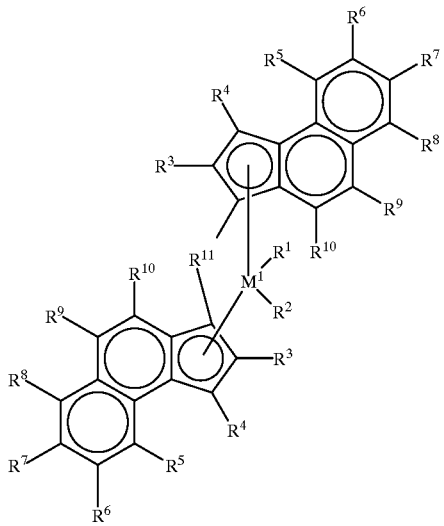

(I)

in which
M$^1$ is a metal of group IVb, Vb or VIb of the periodic table,
R$^1$ and R$^2$ are identical or different and are a hydrogen atom, a C$_1$–C$_{10}$-alkyl group, a C$_1$–C$_{10}$-alkoxy group, a C$_6$–C$_{10}$-aryl group, a C$_6$–C$_{10}$-aryloxy group, a C$_2$–C$_{10}$-alkenyl group, a C$_8$–C$_{40}$-arylalkenyl group, an OH group or a halogen atom,
the radicals R$^3$ are identical or different and are a hydrogen atom, a halogen atom, a C$_1$–C$_{10}$-alkyl group, which can be halogenated, a C$_6$–C$_{10}$-aryl group or an —NR$_2$, —SR, —OSiR$_3$, —SiR$_3$ or —PR$_2$ radical, in which R is a halogen atom, a C$_1$–C$_{10}$-alkyl group or a C$_6$–C$_{10}$-aryl group,
R$^4$ to R$^{10}$ have the meaning given for R$^3$, or adjacent radicals R$^6$ to R$^{10}$, with the atoms joining them form an aromatic or aliphatic ring, and
R$^{11}$ is

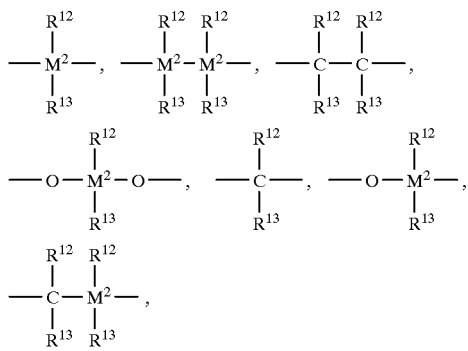

=BR$^{12}$, =AlR$^{12}$, —Ge—, —Sn—, —O—, —S—, =SO, =SO$_2$, =NR$^{12}$, =CO, =PR$^{12}$ or =P(O)R$^{12}$
in which
R$^{12}$ is a hydrogen atom, a halogen atom, a C$_1$–C$_{10}$-alkyl group, a C$_1$–C$_{10}$-fluoroalkyl group, a C$_6$–C$_{10}$-aryl group, a C$_6$–C$_{10}$-fluoroaryl group, a C$_1$–C$_{10}$-alkoxy group, a C$_2$–C$_{10}$-alkenyl group, a C$_7$–C$_{40}$-arylalkyl group, a C$_8$–C$_{40}$-arylalkenyl group or a C$_7$–C$_{40}$-alkylaryl group,
R$^{13}$ is a hydrogen atom, a halogen atom, a C$_4$–C$_{10}$-alkyl group, a C$_1$–C$_{10}$-fluoroalkyl group, a C$_6$–C$_{10}$-aryl group, a C$_6$–C$_{10}$-fluoroaryl group, a C$_1$–C$_{10}$-alkoxy group, a C$_2$–C$_{10}$-alkenyl group, a C$_7$–C$_{10}$-arylalkyl group, a C$_8$–C$_{40}$-arylalkenyl group or a C$_7$–C$_{40}$-alkylaryl group, or R$^{12}$ and R$^{13}$, in each case with the atoms joining the form a ring, and
M$^2$ is silicon, germanium or tin.

2. A process as claimed in claim 1, wherein an aluminoxane of the formula (II)

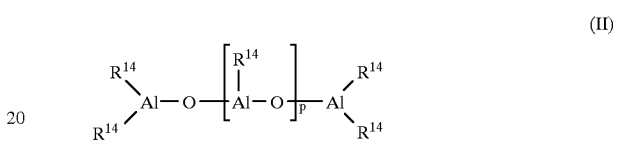

(II)

for the linear type, and/or of the formula (III)

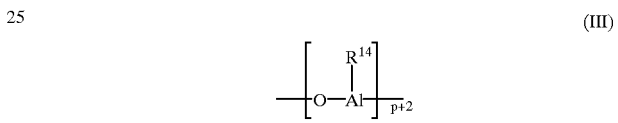

(III)

for the cyclic type, in which, in the formulae (II) and (III), the radicals R$^{14}$ are identical or different and are a C$_1$–C$_6$-alkyl or a C$_6$–C$_{18}$-aryl group, benzyl or hydrogen and p is an integer from 2 to 50, is used as the cocatalyst.

3. The process as claimed in claim 2, wherein the metallocene of the formula I is preactivated with an aluminoxane of the formula II and/or III before use in the polymerization reaction.

4. The process as claimed in claim 1, wherein methylaluminoxane is used as the cocatalyst.

5. The process as claimed in claim 1, wherein the radicals R$^3$ are identical or different and are a hydrogen atom, a halogen atom, a C$_1$–C$_3$-alkyl which is halogenated, a (C$_6$–C$_{10}$)-aryl group or an —NR$_2$, —SR, —OSiR$_3$, —SiR$_3$ or —PR$_2$ radical, in which R is a halogen atom, a C$_1$–C$_{10}$-alkyl group or a C$_6$–C$_{10}$aryl group.

6. The process as claimed in claim 5, wherein the radicals R$^3$ are identical or different and are a hydrogen atom, a halogen atom, a C$_6$–C$_{10}$-aryl group.

7. The process as claimed in claim 5, wherein R$^3$ are identical or different and are —NR$^2$, —SR, —OSiR$_3$, —SiR$_3$ or —PR$_2$ radical, in which R is a halogen atom, a C$_1$–C$_{10}$-alkyl group or a C$_6$–C$_{10}$-aryl group.

8. The process as claimed in claim 1, wherein the radicals R$^4$ are identical or different and are a halogen atom, a C$_1$–C$_3$-alkyl which is halogenated, a (C$_6$–C$_{10}$)-aryl group or an —NR$_2$, —SR, —OSiR$_3$, —SiR$_3$ or —PR$_2$ radical, in which R is a halogen atom, a C$_1$–C$_{10}$-alkyl group or a C$_6$–C$_{10}$-aryl group.

9. The process are claimed in claim 1, wherein R$^1$ and R$^2$ are identical or different and are a hydrogen atom, a C$_1$–C$_{10}$-alkoxy group, a C$_6$–C$_{10}$-aryl group, a C$_6$–C$_{10}$-aryloxy group, a C$_2$–C$_{10}$-alkenyl group, a C$_8$–C$_{40}$-arylalkenyl group or an OH group.

10. The process as claimed in claim 1, wherein the radicals $R^3$ are identical and are a hydrogen atom.

11. The process as claimed in claim 1, wherein at least one of the radicals of $R^5$, $R^6$, $R^7$ and $R^8$ are a halogen atom, a $C_1$–$C_3$-alkyl which is halogenated, a $(C_6$–$C_{10})$-aryl group or an —$NR_2$, —SR, —$OSiR_3$, —$SiR_3$ or —$PR_2$ radical, in which R is a halogen atom, a $C_1$–$C_{10}$-alkyl group or a $C_6$–$C_{10}$-aryl group.

12. The process as claimed in claim 1, wherein the metallocene is methylphenylsilanediylbis(2-methyl-4,5-benzoindenyl)zirconium dichloride or methylphenylsilanediylbis(2-methyl-α-acenaphthindenyl)zirconium dichloride.

13. A process for the preparation of an olefin polymer by polymerization or copolymerization of an olefin of the formula $R^a$—CH═CH—$R^b$, in which $R^a$ and $R^b$ are identical or different and are a hydrogen atom or a hydrocarbon radical having 1 to 14 carbon atoms, or $R^a$ and $R^b$, with the atoms joining them, can form a ring, in the presence of a catalyst which is formed from a metallocene, as the transition metal compound, and a cocatalyst, which comprises using a compound of the formula I

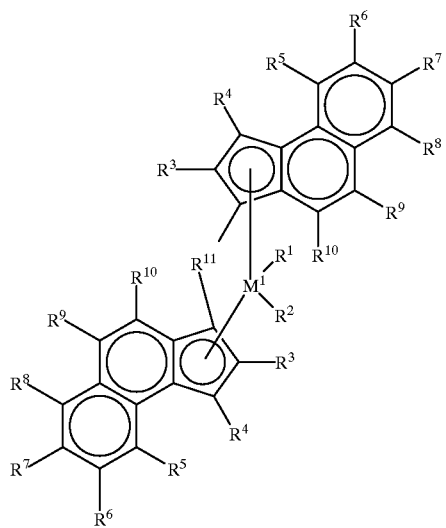

(I)

in which
   $M^1$ is a metal of group IVb, Vb or VIb of the periodic table,
   $R^1$ and $R^2$ are identical or different and are a hydrogen atom, a $C_1$–$C_{10}$-alkyl group, a $C_1$–$C_{10}$-alkoxy group, a $C_6$–$C_{10}$-aryl group, a $C_6$–$C_{10}$-aryloxy group, a $C_2$–$C_{10}$-alkenyl group, a $C_8$–$C_{40}$-arylalkenyl group, an OH group or a halogen atom,
   the radicals $R^3$ are identical or different and are a hydrogen atom, a halogen atom, a $C_4$–$C_{10}$-alkyl group, which can be halogenated, a $C_6$–$C_{10}$-aryl group or an —$NR_2$, —SR, —$OSiR_3$, —$SiR_3$ or —$PR_2$ radical, in which R is a halogen atom, a $C_1$–$C_{10}$-alkyl group or a $C_6$–$C_{10}$-aryl group, $R^4$ to $R^{10}$ are identical or different and are a hydrogen atom, a halogen atom, a $C_1$–$C_{10}$-alkyl group, which can be halogenated, a $C_6$–$C_{10}$-aryl group or an —$NR_2$, —SR, —$OSiR_3$, —$SiR_3$ or —$PR_2$ radical, in which R is a halogen atom, a $C_1$–$C_{10}$-alkyl group or a $C_6$–$C_{10}$-aryl group, or adjacent radicals $R^4$ to $R^{10}$, with the atoms joining them form an aromatic or aliphatic ring, and $R^{11}$ is

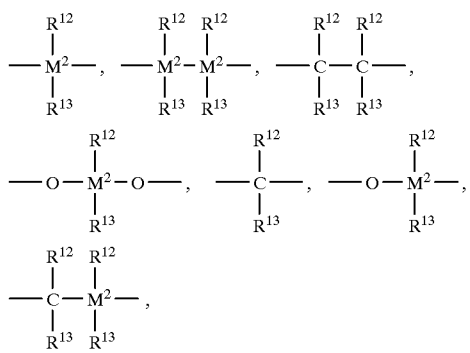

═$BR^{12}$, ═$AlR^{12}$, —Ge—, —Sn—, —O—, —S—, ═SO, ═$SO_2$, ═$NR^{12}$, ═CO, ═$PR^{12}$ or ═P(O)$R^{12}$ in which
   $R^{12}$ and $R^{13}$ are identical or different and are a hydrogen atom, a halogen atom, a $C_1$–$C_{10}$-alkyl group, a $C_1$–$C_{10}$-fluoroalkyl group, a $C_6$–$C_{10}$-aryl group, a $C_6$–$C_{10}$-fluoroaryl group, a $C_1$–$C_{10}$-alkoxy group, a $C_2$–$C_{10}$-alkenyl group, a $C_7$–$C_{40}$-arylalkyl group, a $C_8$–$C_{40}$-arylalkenyl group or a $C_7$–$C_{40}$-alkylaryl group, or $R^{12}$ and $R^{13}$, in each case with the atoms joining the, form a ring, and
   $M^2$ is silicon, germanium or tin.

14. The process as claimed in claim 13, wherein
   $M^1$ is zirconium or hafnium,
   $R^1$ and $R^2$ are identical and are a halogen atom,
   $R^3$ is identical and is a hydrogen or $C_4$–$C_{10}$-alkyl,
   $R^4$–$R^{10}$ are hydrogen and
   $R^{11}$ contains $M^2$ which is silicon.

15. A process for the preparation of an olefin polymer by polymerization or copolymerization of an olefin of the formula $R^a$—CH═CH—$R^b$, in which $R^a$ and $R^b$ are identical or different and are a hydrogen atom or a hydrocarbon radical having 1 to 14 carbon atoms, or $R^a$ and $R^b$, with the atoms joining them, can form a ring, in the presence of a catalyst which is formed from a metallocene, as the transition metal compound, and a cocatalyst, which comprises using a compound of the formula I

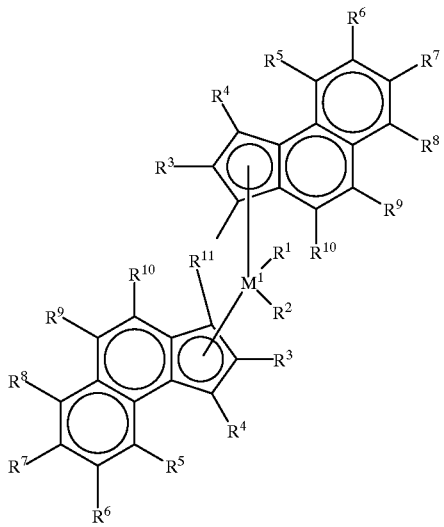

(I)

in which
  $M^1$ is a metal of group IVb, Vb or VIb of the periodic table,
  $R^1$ and $R^2$ are identical or different and are a hydrogen atom, a $C_1$–$C_{10}$-alkyl group, a $C_1$–$C_{10}$-alkoxy group, a $C_6$–$C_{10}$-aryl group, a $C_6$–$C_{10}$-aryloxy group, a $C_2$–$C_{10}$-alkenyl group, a $C_8$–$C_{40}$-arylalkenyl group, an OH group or a halogen atom,
  the radicals $R^3$ are identical or different and are a hydrogen atom, a halogen atom, a $C_1$–$C_{10}$-alkyl group, which can be halogenated, a $C_6$–$C_{10}$-aryl group or an —$NR_2$, —SR, —$OSiR_3$, —$SiR_3$ or —$PR_2$ radical, in which R is a halogen atom, a $C_1$–$C_{10}$-alkyl group or a $C_6$–$C_{10}$-aryl group,
  $R^4$ to $R^{10}$ have the meaning given for $R^3$, or adjacent radicals $R^4$ to $R^{10}$, with the atoms joining them form an aromatic or aliphatic ring, and
  $R^{11}$ is

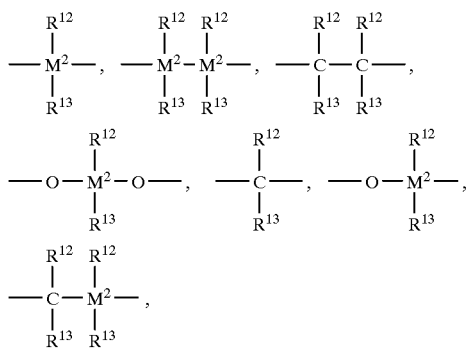

=$BR^{12}$, =$AlR^{12}$, —Ge—, —Sn—, —O—, —S—, =SO, =$SO_2$, =$NR^{12}$, =CO, =$PR^{12}$ or =$P(O)R^{12}$
in which
  $R^{12}$ and $R^{13}$ are identical or different and are a hydrogen atom, a halogen atom, a $C_1$–$C_{10}$-alkyl group, a $C_1$–$C_{10}$-fluoroalkyl group, a $C_6$–$C_{10}$-aryl group, a $C_6$–$C_{10}$-fluoroaryl group, a $C_1$–$C_{10}$-alkoxy group, a $C_2$–$C_{10}$-alkenyl group, a $C_7$–$C_{40}$-arylalkyl group, a $C_8$–$C_{40}$-arylalkenyl group or a $C_7$–$C_{40}$-alkylaryl group, or $R^{12}$ and $R^{13}$, in each case with the atoms joining the, form a ring, and $M^2$ is germanium or tin.

16. The process as claimed in claim 15, wherein the metallocene is 1,2-ethanediylbis(2-methyl-4,5-benzoindenyl)zirconium dichloride.

17. The process as claimed in claim 15, wherein
  $M^1$ is zirconium or hafnium,
  $R^1$ and $R^2$ are identical and are a halogen atom,
  $R^3$ is identical and is a $C_1$–$C_4$-alkyl,
  $R^4$–$R^{10}$ are hydrogen and
  $R^{11}$ contains $M^2$ which is carbon.

18. A process for the preparation of an olefin polymer by polymerization or copolymerization of an olefin of the formula $R^a$—CH=CH—$R^b$, in which $R^a$ and $R^b$ are identical or different and are a hydrogen atom or a hydrocarbon radical having 1 to 14 carbon atoms, or $R^a$ and $R^b$, with the atoms joining them, can form a ring, in the presence of a catalyst which is formed from a metallocene, as the transition metal compound, and a cocatalyst, which comprises using a compound of the formula I

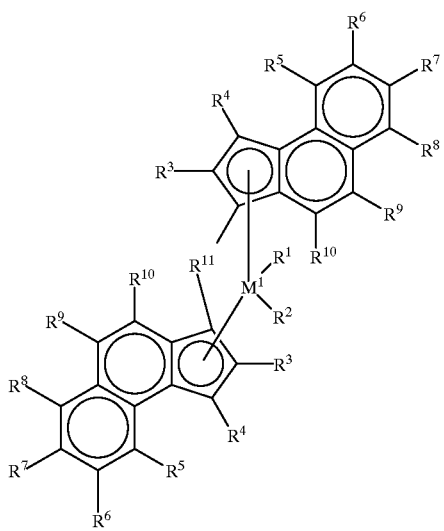

(I)

in which
  $M^1$ is a titanium, hafnium, vanadium, niobium, tantalum, chromium, molybdenum, or tungsten,
  $R^1$ and $R^2$ are identical or different and are a hydrogen atom, a $C_1$–$C_{10}$-alkyl group, a $C_1$–$C_{10}$-alkoxy group, a $C_6$–$C_{10}$-aryl group, a $C_6$–$C_{10}$-aryloxy group, a $C_2$–$C_{10}$-alkenyl group, a $C_8$–$C_{40}$-arylalkenyl group, an OH group or a halogen atom,
  the radicals $R^3$ are identical or different and are a hydrogen atom, a halogen atom, a $C_1$–$C_{10}$-alkyl group, which can be halogenated, a $C_6$–$C_{10}$-aryl group or an —$NR_2$, —SR, —$OSiR_3$, —$SiR_3$ or —$PR_2$ radical, in which R is a halogen atom, a $C_1$–$C_{10}$-alkyl group or a $C_6$–$C_{10}$-aryl group,
  $R^4$ to $R^{10}$ have the meaning given for $R^3$, or adjacent radicals $R^4$ to $R^{10}$, with the atoms joining them form an aromatic or aliphatic ring, and $R^{11}$ is

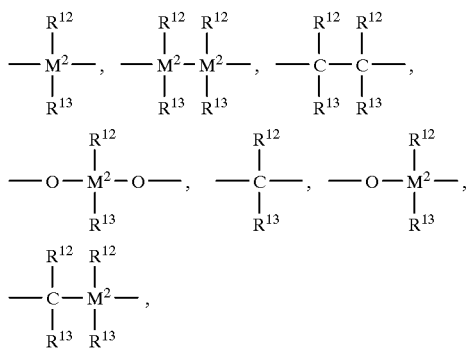

$=BR^{12}, =AlR^{12}, -Ge-, -Sn-, -O-, -S-, =SO,$
$=SO_2, =NR^{12}, =CO, =PR^{12}$ or $=P(O)R^{12}$
in which $R^{12}$ and $R^{13}$ are identical or different and are a hydrogen atom, a halogen atom, a $C_1-C_{10}$-alkyl group, a $C_1-C_{10}$-fluoroalkyl group, a $C_6-C_{10}$-aryl group, a $C_6-C_{10}$-fluoroaryl group, a $C_1-C_{10}$-alkoxy group, a $C_2-C_{10}$-alkenyl group, a $C_7-C_{40}$-arylalkyl group, a $C_8-C_{40}$-arylalkenyl group or a $C_7-C_{40}$-alkylaryl group, or $R^{12}$ and $R^{13}$, in each case with the atoms joining the, form a ring, and $M^2$ is silicon, germanium or tin.

19. The process as claimed in claim 18, wherein the metallocene is dimethylsilanediylbis(2-methyl-α-acenaphthindenyl)zirconium dichloride.

20. The process as claimed in claim 18, wherein
$M^1$ is hafnium,
$R^1$ and $R^2$ are identical and are a halogen atom,
$R^3$ is identical and is a $C_1-C_4$-alkyl,
$R^4-R^{10}$ are hydrogen and
$R^{11}$ contains $M^2$ which is silicon.

* * * * *